United States Patent

Bodor et al.

[11] 4,035,405
[45] July 12, 1977

[54] NOVEL SYNTHESIS FOR PREPARING THE HYDROCHLORIDE SALT OF SELECTED CATECHOLAMINE DERIVATIVES

[75] Inventors: Nicolae S. Bodor, Lawrence, Kans.; Sun-Shine Yuan, Watertown, Mass.

[73] Assignee: Interx Research Corporation, Lawrence, Kans.

[21] Appl. No.: 703,943

[22] Filed: July 9, 1976

[51] Int. Cl.$^2$ .................................. C07C 67/14
[52] U.S. Cl. .................. 260/479 R; 260/295 R; 260/404; 260/468 H; 260/468 R; 260/469; 260/472; 260/473 R; 260/473 G; 260/476 R
[58] Field of Search .................. 260/479 R, 476 R

[56] References Cited

U.S. PATENT DOCUMENTS

| | | | |
|---|---|---|---|
| 3,809,714 | 5/1974 | Hussain et al. | 260/479 R |
| 3,904,671 | 9/1975 | Minatoya et al. | 260/479 R |

Primary Examiner—Lorraine A. Weinberger
Assistant Examiner—Jane T. Fan
Attorney, Agent, or Firm—Charles N. Blitzer

[57] ABSTRACT

Compounds of the formula:

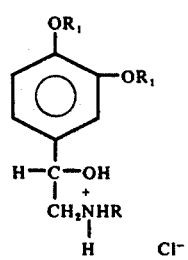

wherein R represents a straight or branched $C_1$-$C_5$ alkyl group; and $R_1$ in each occurrence represents an acyl member which is alkanoyl having 1-22 carbon atoms, alkenoyl having one or two double bonds and having 4-22 carbon atoms,

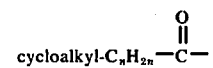

having a total of 4-10 carbon atoms of which 3-7 are ring carbon atoms in cycloalkyl and wherein $n$ is zero, one, or two, phenoxyacetyl, naphthalenecarbonyl, pyridinecarbonyl,

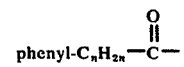

wherein $n$ is zero, one or two and phenyl is unsubstituted or is substituted by 1-3 alkyl having 1-4 carbon atoms, alkoxy having 1-4 carbon atoms, halo, trifluoromethyl, dialkylamino having 2-8 carbon atoms, or alkanoylamino having 1-6 carbon atoms groups; are prepared in substantial purity and yield, using as the chloride ion donor, cesium chloride (CsCl).

The compounds prepared by the process claimed herein exhibit sympathomimetic activity and are thus useful in eliciting sympathomimetic responses in warm-blooded animals, e.g., reduction in intraocular pressure, miosis, mydriasis, bronchodilation, etc.

15 Claims, No Drawings

NOVEL SYNTHESIS FOR PREPARING THE HYDROCHLORIDE SALT OF SELECTED CATECHOLAMINE DERIVATIVES

BACKGROUND OF THE INVENTION

1. Field of the Invention

The present invention is directed to the synthesis of the hydrochloride salt of certain selected catecholamine derivatives. More particularly, the present invention is directed to the use of cesium chloride (CsCl) as the chloride ion donor in the final step for obtaining the hydrochloride salt of the aforementioned compounds.

2. Description of the Prior Art

U.S. Pats. Nos. 3,809,714, 3,825,583, 3,868,461 and pending U.S. patent applications Ser. No. 548,606, filed Feb. 10, 1975 (officially allowed), and Ser. No. 578,079, filed May 16, 1975, all disclose compounds which fall within the above-described generic formula.

A review of these materials will readily show that conventionally, the chloride salt form (which is usually preferred because of its extremely favorable pharmaceutical acceptability) is obtained by first preparing the free base form corresponding to the above generic formula and then treating the free base so obtained with a stoichiometric amount of hydrochloric acid. However, due to the unstable nature of the free base of the above-described compounds, this procedure is quite undesirable as it leads to (1) discoloration, but more importantly, (2) excessive loss of yield and purity of the final product. This is especially true when batch sizes are substantially increased for commercial production.

Accordingly, a need exists for a novel means to prepare the hydrochloride salt of the aforementioned described compounds such that (1) discoloration and (2) excessive loss of yield and purity are minimized.

SUMMARY OF THE INVENTION

It is one object of the present invention to eliminate discoloration in the above-described compounds following synthesis.

It is another object of the present invention to eliminate loss in yield and purity following synthesis of the above-described compounds as well.

All the foregoing objects are achieved by following the step-wise reaction scheme set out below:

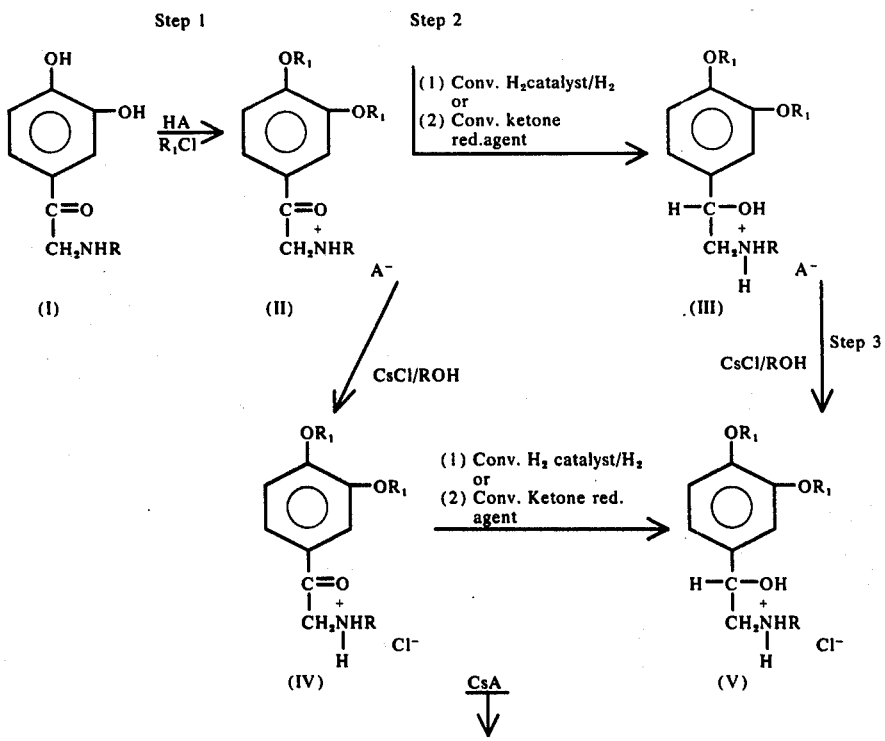

With reference to the above-described reaction scheme, the following definitions and conditions are noteworthy. Substituent "R" represents a straight or branched $C_1-C_5$ alkyl group; substituent "A" represents a $ClO_4^-$ anion, a $CF_3COO^-$ anion or a $R_1-SO_3^-$ anion as defined infra; and substituent "$R_1$" in each occurrence represents an acyl member which is alkanoyl having 1–22 carbon atoms, alkenoyl having one or two double bonds and having 4–22 carbon atoms,

having a total of 4–10 carbon atoms of which 3–7 are ring carbon atoms in cycloalkyl and wherein $n$ is zero, one, or two, phenoxyacetyl, naphthalenecarbonyl, pyridinecarbonyl,

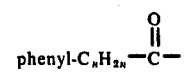

wherein $n$ is zero, one or two and phenyl is unsubstituted or is substituted by 1–3 alkyl having 1–4 carbon atoms, alkoxy having 1–4 carbon atoms, halo, trifluromethyl, dialkylamino having 2–8 carbon atoms, or alkanoylamino having 1–6 carbon atoms groups.

When $R_1$ in applicants' generic formula is alkanoyl containing 1-22 carbon atoms, there are included both unbranched and branched alkanoyl, for example, formyl, acetyl, propionyl, butyryl, isobutyryl, valeryl, isovaleryl, 2-methylbutanoyl, pivalyl, 3-methylpentanoyl, 3,3-dimethylbutanoyl, 2,2-dimethylpentanoyl, docosanoyl, and 7,7-dimethyloctanoyl. The branched alkanoyl groups are preferred over the unbranched alkanoyl groups.

When $R_1$ in applicants' generic formula is alkenoyl having one or two double bonds and having 4-22 carbon atoms, there are included, for example, crotonyl, 9-octadecenoyl, 2,5-hexadienoyl, 3,6-octadienoyl, 10,13-octadecadienoyl, and 5,13-docosadienoyl.

When $R_1$ in applicants' generic formula is

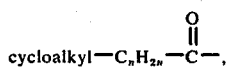

there are included for example the cycloalkanecarbonyl and cycloalkanealkanoyl groups: cyclopropanecarbonyl, 1-methylcyclopropanecarbonyl, cyclopropaneacetyl, alpha-methylcyclopropaneacetyl, 1-methylcyclopropaneacetyl, 2-amylcyclopropaneacetyl, cyclopropanepropionyl, alpha-methylcyclopropanepropionyl, 2-isobutylcyclopropanepropionyl, 2-hexylcyclopropanecarbonyl, cyclobutanepropionyl, 2-methylcyclobutanecarbonyl, 1,3-dimethylcyclobutanecarbonyl, 3,3-dimethylcyclobutanecarbonyl, cyclobutaneacetyl, 2,2-dimethyl-3-ethylcyclobutaneacetyl, cyclobutanepropionyl, cyclopentanecarbonyl, 1-methyl-3-isopropyl, cyclopentanecarbonyl, cyclopentanepropionyl, cyclohexanecarbonyl, cyclohexaneacetyl, 4-methylcyclohexaneacetyl, cycloheptanecarbonyl, 4-methylcycloheptaneacetyl, and cycloheptanepropionyl.

When $R_1$ in applicants' generic formula is

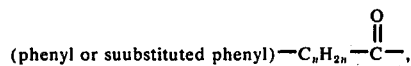

there are included for example benzoyl, phenylacetyl, alpha-phenylpropionyl, beta-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, beta-(p-ethylphenyl)propionyl, p-anisoyl, m-anisoyl, o-anisoyl, m-isopropoxybenzoyl, p-n-butoxybenzoyl, 3-methoxy-4-ethoxybenzoyl, 3,4,5-trimethoxybenzoyl, 2,4,6-triethoxybenzoyl, p-methoxyphenylacetyl, m-isobutoxyphenylacetyl, 3,4-diethoxyphenylacetyl, beta-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, alpha-(m-bromophenyl)propionyl, p-trifluoromethylbenzoyl, 2,4-di(trifluoromethyl)benzoyl, m-trifluoromethylphenylacetyl, beta(p-trifluoromethylphenyl)propionyl, 2-methyl-4-methoxybenzoyl, 3-chloro-4-ethoxybenzoyl, beta-(3-methyl-4-chlorophenyl)propionyl, p-dimethylaminobenzoyl, m-diethylaminobenzoyl, p-dibutylaminobenzoyl, p-(N-methyl-N-ethylamino)-benzoyl, o-acetamidobenzoyl, m-propionamidobenzoyl, p-hexanoylaminobenzoyl, 3-chloro-4-acetamidophenylacetyl, and p-acetamidophenylpropionyl.

When $R_1$ in applicants' generic formula is naphthalenecarbonyl, there are included 1 naphthalenecarbonyl and 2-naphthalenecarbonyl.

When $R_1$ in applicants' generic formula is pyridinecarbonyl, there are included picolinoyl (2-pyridinecarbonyl)nicotinoly(3-pyridinecarbonyl), and isonicotinoyl-(4-pyridinecarbonyl).

Step 1 is run in an inert organic solvent such as ethyl acetate, a chlorinated hydrocarbon solvent (e.g., dichloromethane, dichloroethane, etc.), benzene, toluene, xylene and the like, the reaction being carried out at a temperature between room temperature and the boiling point of the solvent employed, standard pressure and over a period of time ranging from 2 to 12 hours.

In Step 2, two (2) alternative procedures are available. In the first, the product of formula (II) is subjected to hydrogenation in the presence of a catalytic amount of a conventional hydrogenation catalyst such as Pd or $PtO_2$ on charcoal (5-10%) or in the presence of a conventional ketone reducing agent such as $LiAH_4$. The reaction is run in the presence of a $C_1$-$C_5$ alkanol at room temperature, a pressure of from one to three atmospheres and over a period of time of from 1 to 12 hours. In the second alternative procedure, the compound of formula (II) is reacted with CsCl in the presence of an ROH solvent (methanol preferred), wherein R is defined as above to obtain the adrenalone compound IV. This reaction is run at a temperature ranging from 0° C to room temperature, standard pressure, and over a period of time ranging from 1 to 4 hours. The synthesis of compound IV is also deemed novel and is claimed herein as well.

In Step 3, again, two alternative procedures are available. In the first, the compound of formula (III) is reacted with CsCl in the presence of an ROH solvent (methanol preferred), wherein R is defined above. The reaction is carried out at a temperature ranging from 0° C to room temperature, standard pressure and over a period of time of from one to four hours. In the alternative procudure, the compound of formula (IV) is subjected to hydrogenation as outlined earlier with respect to Step 2 in the further presence of CsA, wherein A is defined as above. The reaction is run in the presence of a $C_1$-$C_5$ alkanol, at room temperature, a pressure of from one to three atmospheres and over a period of time ranging from one to twelve hours to obtain the final salt form described by formula (V).

In reference to all synthesis steps described above, with the exception of the acylating agent employed in Step 1, i.e., $R_1$ Cl, all reactants are emplyed in a stoiochiometric amount. The acylating agent is always employed in an excess amount.

Without further elaboration, it is believed that one of ordinary skill in the art can, using the preceding description, utilize the instant invention to its fullest extent. Accordingly, the following preferred specific embodiments are, therefore, to be construed as merely illustrative and not limitative of the remainder of the specification and claims in any way whatsoever. Unless otherwise indicated, all temperature limitations refer to Centigrade.

EXAMPLE I

Preparation of d,l-m-m,p-Dipivalylepinephrine Hydrochloride (This Application)

Step 1 m,p-Dipivalyladrenalone hydroperchlorate

To a mixture of 217.5 g (1.0 mol) adrenalone hydrochloride in 1.5 l ethyl acetate containing 2 l pivalyl chloride was added dropwise with stirring 143 g of 70% perchloric acid. The mixture was heated under reflux for 5 hours. Upon cooling to room temperature, the yellow solution afforded a white crystalline solid which was isolated by filtration. Trituration of this material in anhydrous ether gave 330.2 g (0.73 mol), 73%, m,p-dipivalyladrenalone hydroperchlorate, mp 174°–176°; ir (KBr) 3200, 2960, 1750, 1705, 1595 and 1050 cm$^{-1}$; pmr (CD$_3$COCD$_3$) δ 8.2 (bs, 2H), 8.0–7.4 (AB, 2H), 7.9 (s, 1H), 5.0 (t, 2H) and 1.3 (s, 18H) ppm.

Anal. Calcd for C$_{19}$H$_{28}$ClNO$_9$: C, 50.72; H, 6.27; N, 3.11. Found: C, 50.80; H, 6.24; N, 3.12.

Step 2 d,l-m,p-Dipivalylepinephrine hydroperchlorate 33.3 g (0.074 mol) m,p-dipivalyladrenalone hydroperchlorate was dissolved in 300 ml ethanol, 1.5 g platinum oxide was added and the mixture was shaken under a hydrogen pressure of 50 psi for 4 hours. Following filtration, the ethanol was removed under reduced pressure to afford an oily residue. Crystallization from anhydrous ether gave 33 g (0.073 mol), 99%, d,l-m,p-dipivalylepinephrine hydroperchlorate, mp 148°–149°; ir (KBr) 3600, 3200, 1755, 1605 and 1120 cm$^{-1}$; pmr (CD$_3$COCD$_3$) δ 8.0 (bs, 2H), 7.5–7.1 (AB, 2H), 7.3 (s, 1H), 5.3 (m, 2H), 3.2 (m, 2H), 3.1 (s, 3H) and 1.4 (s, 18H) ppm.

Anal. Calcd for C$_{19}$H$_{30}$ClNO$_9$: C, 50.49; H, 6.64; N, 3.10. Found: C, 50.79; H, 6.72; N, 2.65.

Step 3 d,l-m,p-Dipivalylepinephrine hydrochloride 45.2 g (0.1 mol) d,l-m,p-dipivalylepinephrine hydroperchlorate was dissolved in 250 ml methanol and stirred at 0° while 16.9 g (0.1 mol) cesium chloride in 750 ml methanol was added dropwise. After stirring 1 hour at 0°, the cesium perchlorate was removed by filtration and the methanol removed under reduced pressure. Recrystallization from acetone petroleum ether gave 32.3 g (0.083 mol), 83%, d,l-m,p-dipivalylepinephrine hydrochloride, mp 159°–160°, ir (KBr) 3280, 2960, 2800, 1750, 1250, 1100 and 980 cm$^{-1}$; pmr (CDCl$_3$) δ 7.6–6.9 (m, 3H), 5.4 (m, 1H), 3.2 (b, 2H), 2.7 (s, 3H) and 1.3 (s, 18H) ppm.

Anal. Calcd for C$_{19}$H$_{30}$ClNO$_5$: C, 58.82; H, 7.80; N, 3.61. Found: C, 58.34; H, 7.86; N, 4.01.

EXAMPLE II

Preparation of d,l-m,p-Dipivalylepinephrine Hydrochloride (Alternative Route - This Application)

Step 1

Preparation of m,p-Diivalyladrenalone hydrochloride

To a methanol solution containing 44.7 g (0.099 mol) m,p-dipivalyladrenalone hydroperchlorate at 0° was added dropwise with stirring a methanol solution containing 16.7 g (0.099 mol) cesium chloride. After stirring for 0.5 hr at 0°, the cesium perchlorate was removed by filtration and the methanol filtrate was concentrated under reduced pressure to a light yellow solid. Recrystallization of isopropanol gave 23.1 g (0.060 mol), 60%, m,p-dipivalyladrenalone hydrochloride, mp 201°–203°, tlc [silica gel/chloroform:methanol:formic acid:30:10:1 (VIV)] R$_f$=0.65, uv (methanol): λmax 254 nm, λ 280 nm (sh); ir (KBr) 2980, 2770, 1750, 1685, 1260, 1100 and 840 cm$^{-1}$; pmr (CD$_3$COCD$_3$.D$_2$O) δ 6.8 – 7.7 (m, 3H), 4.4 (s, 2H), 2.5 (s, 3H) and 0.9 (s, 18H) ppm.

Anal. Calcd for C$_{19}$H$_{28}$ClNO$_5$: C, 59.13; H, 7.31; N, 3.63; Cs, trace. Found: C, 59.19; H, 7.22; N, 3.76, Cs, 99 ppm.

Step 2

Preparation of d,l-m,p-Dipivalylepinephrine hydrochloride 38.6 g (0.1 mol) m,p-dipivalyladrenalone hydrochloride was dissolved in 300 ml methanol, 1.0 g platinum oxide was added and the mixture was shaken under a hydrogen pressure of 50 psi for 4 hours. Following filtration, the methanol was removed under reduced pressure. Recrystallization from acetone:petroleum ether gave 32.9 g (0.085 mol), 85%, d,l-m,p-dipivalylepinephrine hydrochloride, mp 159°–160°, ir (KBr) 3280, 2960, 2800, 1750, 1250, 1100 and 980 cm$^{-1}$; pmr (CDCl$_3$) δ 7.6–7.9 (m, 3H), 5.4 (m, 1H), 3.2 (b, 2H), 2.7 (s, 3H) and 1.3(s, 18H) ppm.

Anal. Calcd for C$_{19}$H$_{30}$ClNO$_5$: C, 58.82; H, 7.80; N, 3.61. Found: C, 58.69; H, 8.00; N, 3.60.

PREPARATION OF d,l-m,p-DIPIVALYLEPINEPHRINE HYDROCHLORIDE (PRIOR ART)

d,l-m,p-Dipivalylepinephrine hydrochloride 50 g (0.11 mol) d,l-m,p-dipivalylepinephrine hydroperchlorate was dissolved in 900 ml of warm water and stirred at 0° under nitrogen while one equivalent of ammonia was added (ammonium hydroxide, 58%, specific gravity 0.90). The solution (pH 8–9) was extracted with ether. The ether extracts were combined and dried over anhydrous magnesium sulfate. Following filtration, the filtrate at 0° was saturated with anhydrous hydrogen chloride. Removal of the solvent under reduced pressure gave an amorphous solid. Recrystallation of this material from ethyl acetate hexane gave 21.3 g (0.055 mol), 50%, d, 1-m,p-dipivalylepinephrine hydrochloride, mp 159°–161°.

Anal. Calcd for C$_{19}$H$_{30}$ClNo$_5$: C, ;b 58.82; H, 7.80; N, 3.61.

Found: C, 59.20; H, 8.12; N, 3,36.

By following the foregoing example and substituting the generically and/or specifically described reactants and/or operative conditions, the following compounds of formulas IV and V are prepared in substantially similar yield and purity:

1. d,1-m,p-diacetylepinephrine hydrochloride
2. d,1-m,p-ditoluylepiniphrine hydrochloride
3. d,1-m,p-diisolvalerylepinephrine hydrochloride
4. d,1-m,p-di(phenylacetyl)epinephrine hydrochloride
5. d,1-m,p-di(cyclohexanecarboxyl)epinephrine hydrochloride
6. d,1-m,p-di-(2,2-dimethylpenanoyl)epinephrine hydrochloride
7. d,1-m,p-di(cyclohexaneacetyl)epinephrine hydrochloride
8. d,1-m,p-di(p-ethoxybenzoyl)epinephrine hydrochloride
9. d,1-m,p-p-dipivalylnorepinephrine hydrochloride
10. d,1-m,p-diacetylnorepinephrine hydrochloride
11. d,1-m,p-ditoluylnorepinephrine hydrochloride
12. d,1m,p-diisovalerylnorepinephrine hydrochloride 13. d,1-m,p-di(phenylacetyl)norepinephrine hydrochloride
14. d,1-m,p-di(cyclohexanecarboyl)norepinephrine hydrochloride
15. d,1-m,p-di(2,2-dimethylpentanoyl)norepinephrine hydrochloride
16. d,1-m,p-di(cyclohexanacetyl)norepinephrine hydrochloride
17. d,1-m,p-de(p-ethoxybenzoyl)norepinephrine hydrochloride
18. d,1-m,p-dipivalyladrenalone hydrochloride
19. d,1-m,p-diacetyladrenalone hydrochloride
20. d,1-m,p-ditoluyladrenalone hydrochloride
21. d,1-m,p-diisovalerylladrenalone hydrochloride
22. d,1-m,-di(phenylacetyl)adrenalone hydrochloride
23. d,1-m,p-di(cyclohexanecarboxyl)adrenalone hydrochloride
24. d,1-m,p-di(2,2-dimethylpentanoyl)arednalone hydrochloride
25. d,1-m,p-di(cyclohexaneacetyl)adrenalone hydrochloride
26. d,1-m,p-di(p-ethoxybenzoyl)adrenalone hydrochloride
27. d,1-m,p-dipivalylisoproterenol hydrochloride
28. d,1-m,p-diacetylisopropterenol hydrochloride
29. d,1-m,p-ditoluylisoproterenol hydrochloride
30. d,1-m,p-diisovalerylisoproterenol hydrochloride
31. d,1-m,p-di(phenylacetyl)isoproterenol hydrochloride
32. d,1-m,p-di(cyclohexanecarboxyl)isoproterenol hydrochloride
33. d,1-m,p-di(2,2-dimethylpentanoyl)isoproterenol hydrochloride
34. d,1m,p-di(cyclohexaneacetyl(isoproterenol hydrochloride
35. d,1-m,p-di(p-ethoxybenzoyl)isoproterenol hydrochloride As one can readily observe, the process of the present invention offers a decided advantage over the prior art from the standpoint of purity and yield. Substantially similar results will be obtained when applying the process of the present invention to the remaining compounds generically described herein.

The compounds prepared by the process of the instant invention can be used by the pharmaceutical and/or veterinary arts for the treatment of glaucoma, bronchial asthma, and nasal decongestion associated with hay fever and allergic rhinitis in warm-blooded animals (e.g., humans) in a variety of pharmaceutical preparations as described in U.S. Pat. Nos. 3,809,714, 3,825,583, 3,868,461 and pending U.S. patent applications, Ser. No. 548,606, filed Feb. 10, 1975 (officially allowed), and Ser. No. 578,079, filed May. 16, 1975, respectively.

As for the therapeutic dose required of the compounds prepared by the process of the instant invention, while dosage limitations will naturally vary with the size and needs of the individual treated, normally, the dosage range will usually be an effective amount, or the equivalent on a molar basis of the pharmacologically active form produced upon the metabolic release of the active drug to achieve its desired pharmacological and physiological effect.

From the foregoing description, one of ordinary skill in the art can easily ascertain the essential characteristics of this invention, and without departing from the spirit and scope thereof, can make various changes and/or modifications of the invention to adapt it to various usages and conditions. As such, these changes and/or modifications are properly, equitably, and intended to be, within the full range of equivalents of the following claims.

What we claim is:

1. A method for preparing a compound of the formula:

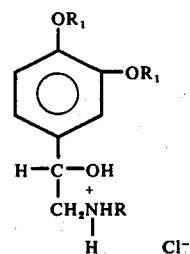

which comprises the steps of:

A. reacting, in the presence of an inert organic solvent, a compound having the formula:

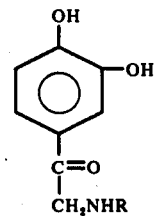

with an acid designated as HA and an acylating agent designated as $R_1Cl$ to thus obtain a compound having the formula:

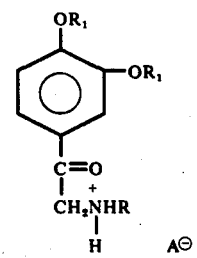

B. subjecting, in the presence of a $C_1$–$C_5$ alkanol, the compound obtained from step (A) to hydrogenation in the presence of a catalytic amount of a conventional hydrogenation catalyst or an effective amount of a conventional ketone reducing agent to obtain a compound having the formula:

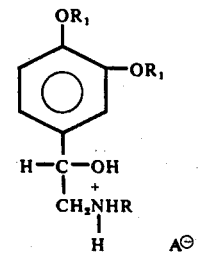

C. reacting the compound obtained from step (B) with CsCl and an ROH alcohol to thus obtain the final compound; and D. separating the final compound thus obtained in step (C) from the reaction mixture, wherein R represents a straight or branched $C_1$-$C_5$ alkyl group; wherein $R_1$ represents an acyl member which is alkanoyl having 1-22 carbon atoms, alkenoyl having one or two double bonds and having 4-22 carbon atoms,

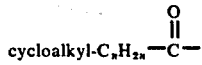

having a total of 4-10 carbon atoms of which 3-7 are ring carbon atoms in cycloalkyl and wherein n is zero, one, or two, phenoxyacetyl, naphthalenecarbonyl, pyridinecarbonyl,

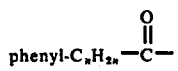

wherein n is zero, one or two and phenyl is unsubstituted or is substituted by 1-3 alkyl having 1-4 carbon atoms, alkoxy having 1-4 carbon atoms, halo, trifluoromelthyl, dialkylamino having 2-8 carbon atoms, or alkanoylamino having 1-6 carbon atom groups; and wherein A represents a $ClO_4^-$ anion, a $CF_3COO^-$ anion or a $R_1$-$SO_3^-$ anion, wherein $R_1$ is defined as above.

2. The method of claim 1, wherein the inert organic solvent employed in step (A) is a member selected from the group consisting of ethyl acetate, a chlorinated hydrocarbon, benzene, toluene or xylene.

3. The method of claim 1, wherein the hydrogenation catalyst employed in step (B) is a member selected from the group consisting of Pd or $PtO_2$ on charcoal (5-10%).

4. The method of claim 1, wherein the reducing agent employed in step (B) is $LiAH_4$.

5. The method of claim 1, wherein in step (B), the ROH alcohol employed in step (C) is methanol.

6. The method of claim 1, wherein the compound prepared is: d,1m,p-Dipivalylepinephrine hydrochloride.

7. A method for preparing a compound of the formula:

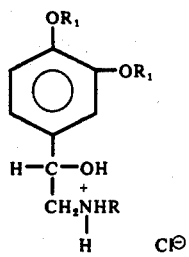

which comprises the steps of:
A. reacting, in the presence of an inert organic solvent, a compound of the formula:

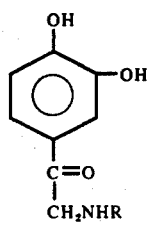

with an acid designated as HA and an acylating agent designated as $R_1Cl$ to thus obtain a compound of the formula:

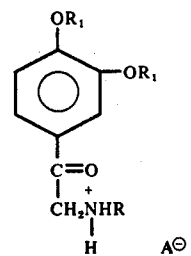

B. reacting the final compound obtained from step (A) with CsC1 and an ROH alcohol to thus obtain a compound having the formula:

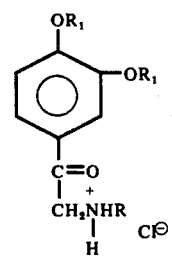

C. subjecting, in the presence of a $C_1$-$C_5$ alkanol, the final compound of step (B) to hydrogenation in the presence of a compound designated as CsA to thus obtain the final compound desired; and D. separating the final compound so obtained in step (C) from the reaction mixture, wherein R represents a straight or branched $C_1$-$C_5$ alkyl group, wherein $R_1$ represents an acyl member which is alkanoyl having 1-22 carbon atoms, alkenoyl having one or two double bonds and having 4-22 carbon atoms,

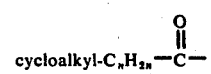

having a total of 4-10 carbon atoms of which 3-7 are ring carbon atoms is cycloalkyl and wherein n is zero, one, or two, phenoxyacetyl, naphthalenecarbonyl, pryidinecarbonyl,

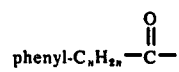

wherein n is zero, one or two and phenyl is unsubstituted or is substituted by 1-3 alkyl having 1-4 carbon atoms, alkoxy having 1-4 carbon atoms, halo, trifluoromethyl, dialkylamino having 2-8 carbon atoms, or alkanoylamino having 1-6 carbon atom groups; and wherein A represents a $ClO_4^-$ anion a $CF_3COO^-$ anion or a $R_1$—$SO_3^-$ anion, wherein $R_1$ is defined as above.

8. The method of claim 7, wherein the inert organic solvent employed for step (A) is a member selected from the group consisting of ethyl acetate, a chlorinated hydrocarbon, dichloromethane, benzene, toluene or xylene.

9. The method of claim 7, wherein the hydrogenation catalyst employed in step (C) is a member selected from the group consisting of Pd or PtO₂ on charcoal (5–10%).

10. The method of claim 7, wherein step (B), the ROH alcohol employed is methanol.

11. The method of claim 7, wherein the final compound prepared is: d,1-m,p-Dipivalylepinephrine hydrochloride.

12. A method for preparing a compound of the formula:

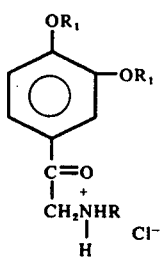

which comprises the steps of:

A. reacting, in the presence of an inert organic solvent, a compound of the formula:

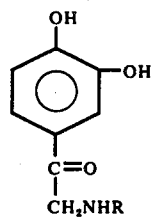

with an acid designated as HA and an acylating agent designated as R₁Cl to thus obtain a compound of the formula:

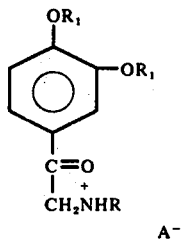

B. reacting the final compound obtained from step (A) with CsCl and an ROH alcohol to thus obtain the final compound, and C. separating the final compound so obtained in step (B) from the reaction mixture, wherein R represents a straight or branched $C_1-C_5$ alkyl group; wherein $R_1$ represents an acyl member which is alkanoyl having 1–22 carbon atoms, alkenoyl having one or two double bonds and having 4–22 carbon atoms,

having a total of 4–10 carbon atoms of which 3–7 are ring carbon atoms in cycloalkyl and wherein n is zero, one, or two, phenoxyacetyl, naphthalenecarbonyl, pyridinecarbonyl,

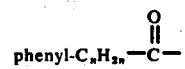

wherein n is zero, one or two and phenyl is unsubstituted or is substituted by 1–3 alkyl having 1–4 carbon atoms, alkoxy having 1–4 carbon atoms, halo, trifluoromethyl, dialkylamino having 2–8 carbon atoms, or alkanoylamino having 1–6 carbon atom groups; and wherein A represents a $ClO_4^-$ anion, a $CF_3COO^-$ anion or a $R_1—SO_3^-$ anion, wherein $R_1$ is defined as above.

13. The method of claim 12, wherein the inert organic solvent in step (A) is a member selected from the group consisting of ethyl acetate, a chlorinated hydrocarbon, benzene, toluene or xylene.

14. The method of claim 12, wherein in step (B), the ROH alcohol is methanol.

15. The method of claim 12, wherein the compound prepared is: d,1-m,p-dipivalyladrenalone hydrochloride.

* * * * *

UNITED STATES PATENT OFFICE
CERTIFICATE OF CORRECTION

Patent No. 4,035,405          Dated July 12, 1977

Inventor(s) Nicolae S. Bodor and Sun-Shine Yuan

It is certified that error appears in the above-identified patent and that said Letters Patent are hereby corrected as shown below:

<u>In Claim 7, step (C):</u>

Delete "a compound designated as CsA" and insert --a catalytic amount of a conventional hydrogenation catalyst or an effective amount of a conventional ketone reducing agent--.

Signed and Sealed this

Sixth Day of December 1977

[SEAL]

*Attest:*

RUTH C. MASON          LUTRELLE F. PARKER
*Attesting Officer*          *Acting Commissioner of Patents and Trademarks*